(12) United States Patent
Maleksadeh

(10) Patent No.: US 6,503,956 B2
(45) Date of Patent: Jan. 7, 2003

(54) DETERMINATION OF HETEROATOM CONTENT IN FISCHER-TROPSCH WAX

(75) Inventor: Nga Maleksadeh, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 09/758,751

(22) Filed: Jan. 11, 2001

(65) Prior Publication Data

US 2002/0090727 A1 Jul. 11, 2002

(51) Int. Cl.⁷ .......................... C07C 27/00; G01N 33/00
(52) U.S. Cl. ........................................ 518/700; 436/60
(58) Field of Search .................. 422/83, 52; 436/60, 436/139, 116, 117, 118; 518/700

(56) References Cited

U.S. PATENT DOCUMENTS

| | | | |
|---|---|---|---|
| 3,032,493 A | 5/1962 | Coulson et al. | |
| 3,852,207 A | 12/1974 | Stangeland et al. | |
| 3,904,513 A | 9/1975 | Fischer et al. | |
| 4,018,562 A | 4/1977 | Parks et al. | 23/230 |
| 4,157,294 A | 6/1979 | Iwao et al. | |
| 4,351,801 A | 9/1982 | Bartke | 422/78 |
| 4,401,556 A | 8/1983 | Bezman et al. | |
| 4,657,661 A | 4/1987 | Miller | |
| 4,820,402 A | 4/1989 | Partridge et al. | |
| 4,913,799 A | 4/1990 | Gortsema et al. | |
| 4,914,037 A | 4/1990 | Forster et al. | 436/106 |
| 5,059,567 A | 10/1991 | Linsten et al. | |
| 5,073,530 A | 12/1991 | Bezman et al. | |
| 5,114,563 A | 5/1992 | Lok et al. | |
| 5,185,268 A * | 2/1993 | Bonometti et al. | 426/114 |
| 5,198,203 A | 3/1993 | Kresge et al. | |
| 5,246,689 A | 9/1993 | Beck et al. | |
| 5,334,368 A | 8/1994 | Beck et al. | |
| 5,501,981 A * | 3/1996 | Ray et al. | 436/123 |
| 5,612,225 A | 3/1997 | Baccanti et al. | 436/114 |
| 5,916,523 A * | 6/1999 | Yan et al. | 422/88 |
| 2001/0021724 A1 | 9/2001 | Arcuri et al. | |

OTHER PUBLICATIONS

Day, D., "A Suggestion as to the Origin of Pennsylvania Petroleum", Proceedings of the American Philosophical Society, 36: 112 (1897).

Gruse, W., and Stevens, D., *Chemical Technology of Petroleum*, 3$^{rd}$ edition: pp. 331–333 (1960) McGraw Hill Book Company, Inc., New York.

* cited by examiner

*Primary Examiner*—Jill Warden
*Assistant Examiner*—Samuel P Siefke
(74) *Attorney, Agent, or Firm*—Burns, Doane, Swecker & Mathis, L.L.P.

(57) ABSTRACT

A method for analyzing the heteroatom content of solid products which spatter, boil or bump under conditions involving rapid heating, such as Fischer-Tropsch heavy products, including Fischer-Tropsch waxes, is disclosed. The heteroatom content of Fischer Tropsch heavy products can be determined by melting the sample prior to injecting into the analytical instrument used for the analysis. This provides results that are reproducible and accurate. The melting can be done, for example, prior to injection, in a syringe, or by placing the sample in a boat and melting it prior to injection. The melting can be effected by simply moving the boat slowly into the chamber which allows sufficient time for the sample to melt before it is exposed to the high temperature of the combustion zone. Nitrogen and sulfur determination are preferably carried out using a chemiluminescent detector that detects chemically-bound nitrogen and/or sulfur. Oxygen detection is preferably carried out using GC/MS.

22 Claims, No Drawings

DETERMINATION OF HETEROATOM CONTENT IN FISCHER-TROPSCH WAX

FIELD OF THE INVENTION

This invention is in the area of chemical analysis of Fischer-Tropsch waxes, in particular, the determination of heteroatom content in Fischer-Tropsch waxes.

BACKGROUND OF THE INVENTION

The majority of combustible fuel used in the world today is derived from crude oil. There are several concerns with using crude oil as a fuel source. Crude oil is includes aromatic compounds believed to cause cancer. It also includes sulfur and nitrogen compounds that add to air pollution upon burning.

Combustible liquid fuels can also be prepared from natural gas. This involves converting the natural gas, which is mostly methane, to synthesis gas (syngas), which is a mixture of carbon monoxide and hydrogen. Fischer-Tropsch chemistry is typically used to convert the syngas to a product stream that includes combustible fuel, among other products.

Fischer-Tropsch chemistry tends to produce a broad spectrum of products, ranging from methane to wax. Product slates for syngas conversion over Fischer-Tropsch catalysts (Fe, Co and Ru) are controlled by polymerization kinetics with fairly constant chain growth probabilities, which fix the possible product distributions. Heavy products with a relatively high wax content are produced when chain growth probabilities are high. Methane is produced with high selectivity when chain growth probabilities are low. While methane can be recirculated to ultimately yield combustible liquid fuel, it is typically preferable to form heavy products such as wax. These heavy products can be processed, for example, by hydrocracking followed by oligomerization, to yield combustible liquid fuel.

The catalytic processes used to convert the heavy products are often sensitive to heteroatom poisons, in particular, sulfur and nitrogen. It is advantageous to determine the heteroatom content of Fischer-Tropsch wax and other heavy products before performing catalytic processes on these products.

Chemiluminescence is a conventional technique for measuring nitrogen content in liquid materials. This technique is described, for example, in U.S. Pat. No. 4,018,562, the contents of which are hereby incorporated by reference. Chromatographic methods have also been used to measure nitrogen content, as described, for example, in U.S. Pat. No. 5,612,225, the contents of which are hereby incorporated by reference.

These techniques are designed for the analysis of liquid materials. The types of solids that can be effectively analyzed are those which form a residue and which do not boil during analysis. Erratic results are obtained if the solid materials boil and spatter during the analysis. Thus, it is not readily apparent that one can analyze certain types of solid materials, especially those which spatter or boil, when using these techniques.

The wax and other heavy products from Fischer-Tropsch synthesis are solid materials that melt at relatively high temperatures, and are often subject to spattering or boiling at these temperatures. For these reasons, the analysis of heteroatom content in Fischer-Tropsch heavy products using conventional techniques is extremely difficult and imprecise.

Various methods have been suggested for analyzing solid materials, including dissolving the solids to form a liquid solution, or directly injecting the solids into the analytical equipment. U.S. Pat. No. 4,914,037 describes a process for dispersing a solid in a cool zone by nebulization. None of these methods provide an effective means for analysis of heteroatom content in Fischer Tropsch heavy products.

It would be desirable to have a method for analyzing the heteroatom content of Fischer-Tropsch heavy products. The present invention provides such a method.

SUMMARY OF THE INVENTION

A method for analyzing the heteroatom content of Fischer-Tropsch wax and other heavy products, in particular, nitrogen-containing, substantially paraffinic products, is disclosed. Among other factors, this invention resides in the realization that pre-heat melting avoids many prior problems and surprisingly permits the extension of heretofore liquids-only techniques to solids analysis.

The heteroatom content of Fischer Tropsch heavy products can be determined by melting the sample prior to injection into the analytical instrument used for the analysis. This provides results that are reproducible and accurate.

The melting can be done in any number of ways. When the sample to be analyzed is to be injected into an analytical apparatus, for example, a gas chromatograph (GC), the sample can be melted in an external apparatus prior to injection, or melted in a syringe. Another method is to place the sample in a suitable device, for example, a boat and melt it prior to injection. The melting can be effected by simply moving the device slowly into a heated chamber which allows sufficient time for the sample to melt before it is exposed to the relatively high temperature of the combustion zone, as used in various analytical equipment.

Nitrogen and sulfur determination is preferably carried out using a chemiluminescence detector that detects chemically-bound nitrogen and sulfur. Preferred samples to be analyzed include wax directly obtained from a Fischer-Tropsch synthesis or distilled from a portion of the product of a Fischer-Tropsch synthesis. The wax can also be hydrogenated, denitrified, hydrocracked and/or hydrodesulfurized.

DETAILED DESCRIPTION OF THE INVENTION

A method for analyzing the heteroatom content of Fischer-Tropsch wax and other heavy products, in particular, nitrogen-containing, substantially paraffinic products, is disclosed. The heteroatom content of Fischer Tropsch wax and other heavy products is determined by melting the sample prior to injecting into the analytical instrument used for the analysis. Preferred samples to be analyzed include wax directly obtained from a Fischer-Tropsch synthesis or distilled from a portion of the product of a Fischer-Tropsch synthesis. The wax can also be hydrogenated, denitrified, hydrocracked and/or hydrodesulfurized.

Fischer-Tropsch waxes and other heavy products tend to be substantially paraffinic and may include significant amounts of nitrogen to adversely affect catalysts used to further refine these products, and it is advantageous to reduce the nitrogen content of these products below a threshold value. The terms "nitrogen-containing" and "nitrogen-containing, substantially paraffinic product," as used herein, refers to a product comprising at least 50% paraffins and at least 1 ppm nitrogen. Unless otherwise specified, all percentages are in weight percent and all parts per million (ppm) are by weight.

When the Fischer-Tropsch products contain nitrogen, the conditions used to reduce the nitrogen content preferably reduce the amount to below about 15 ppm, preferably below 5 ppm, and more preferably, below about 1 ppm. This typically requires that the sample be analyzed both before and after denitrification, to ensure that the denitrification method was successful. Typical methods for denitrification involve hydrotreating, adsorption and extraction.

In Fischer-Tropsch chemistry, syngas is converted to hydrocarbons by contact with a Fischer-Tropsch catalyst under reactive conditions. The Fischer-Tropsch reaction may be effected in a fixed bed, in a slurry bed, or in a fluidized bed reactor. The Fischer-Tropsch reaction conditions may include using a reaction temperature of between 190?C and 340?C, with the actual reaction temperature being largely determined by the reactor configuration. Thus, when a fluidized bed reactor is used, the reaction temperature is preferably between 300?C and 340?C; when a fixed bed reactor is used, the reaction temperature is preferably between 200?C and 250?C; and when a slurry bed reactor is used, the reaction temperature is preferably between 190?C and 270?C.

An inlet synthesis gas pressure to the Fischer-Tropsch reactor of between 1 and 50 bar, preferably between 15 and 50 bar, may be used. The synthesis gas may have a $H_2$:CO molar ratio, in the fresh feed, of 1.5:1 to 2.5:1, preferably 1.8:1 to 2.2:1. The synthesis gas typically includes 0.1 wppm of sulfur or less. A gas recycle may optionally be employed to the reaction stage, and the ratio of the gas recycle rate to the fresh synthesis gas feed rate, on a molar basis, may then be between 1:1 and 3: 1, preferably between 1.5:1 and 2.5:1. A space velocity, in $m^3$ (kg catalyst)$^{-1}$ hour$^{-1}$, of from 1 to 20, preferably from 8 to 12, may be used in the reaction stage.

In principle, an iron-based, a cobalt-based or an iron/cobalt-based FischerTropsch catalyst can be used in the Fischer-Tropsch reaction stage. The iron-based Fischer-Tropsch catalyst may include iron and/or iron oxides which have been precipitated or fused. However, iron and/or iron oxides which have been sintered, cemented, or impregnated onto a suitable support can also be used. The iron should be reduced to metallic Fe before the Fischer-Tropsch synthesis. The iron-based catalyst may contain various levels of promoters, the role of which may be to alter one or more of the activity, the stability, and the selectivity of the final catalyst.

Preferred promoters are those influencing the surface area of the reduced iron ('structural promoters'), and these include oxides or metals of Mn, Ti, Mg, Cr, Ca, Si, Al, or Cu or combinations thereof.

The products directly from Fischer-Tropsch reactions, before cooling to room temperature, generally include a gaseous reaction product and a liquid reaction product. The gaseous reaction product includes hydrocarbons boiling below about 650° F (e.g., tail gases through middle distillates). The liquid reaction product (the wax fraction) includes hydrocarbons boiling above about 650° F. (e.g., vacuum gas oil through heavy paraffins).

Commercially, the product boiling below about 650° F. is typically separated into a tail gas fraction (including $C_{14}$ olefins and paraffins) and a condensate fraction, i.e., about $C_5$ to $C_{20}$ normal paraffins and higher boiling hydrocarbons. The fraction boiling above about 650° F. (the wax fraction) typically contains $C_{20}$ to $C_{50}$ linear paraffins with relatively small amounts of higher boiling branched paraffins.

Catalysts with relatively high chain growth probabilities (for example, an alpha value above about 0.8) favor formation of wax and other heavy products, and tend to form relatively low amounts of methane. The wax can be treated, for example, by hydrocracking and other refinery techniques, to provide a variety of products. The methods described herein permit the rapid analysis of the heteroatom content of the wax fraction and other solid products derived in whole or in part from the wax fraction.

Catalytic refining techniques for converting Fischer-Tropsch wax and heavier hydrocarbon products to lower molecular weight products typically involve contacting the hydrocarbons with hydrogen gas in the presence of a zeolite or other molecular sieve catalyst. The catalytic refining methods for treating the heavier hydrocarbons are well known to those of skill in the art, and typically involve the use of catalytic zeolites and other catalytic molecular sieves.

Zeolite and other molecular sieve catalysts are typically sensitive to the presence of heteroatoms such as nitrogen and sulfuir. However, measuring these heteroatoms in wax was heretofore difficult, if at all possible. While certain amounts of these heteroatoms can be tolerated, it is generally preferred to determine the amount of these impurities before subjecting them to the catalytic refining techniques.

Methods for removing heteroatoms from hydrocarbons are well known to those of skill in the art, and include hydrotreating, adsorption and extraction, provided their existence was acknowledged. If the hydrocarbons include too high a level of impurities, such methods can be employed before subjecting the hydrocarbons to the catalytic refining techniques.

Hydrogenation catalysts can be used for the purification. For example, a noble metal from Group VIIIA according to the 1975 rules of the International Union of Pure and Applied Chemistry, such as platinum or palladium on an alumina or siliceous matrix, or unsulfided Group VIIIA and Group VIB, such as nickel-molybdenum or nickel-tin on an alumina or siliceous matrix, is a suitable catalyst. U.S. Pat. No. 3,852,207 to Stangeland et al. "Production of Stable Lubricating Oils by Sequential Hydrocracking and Hydrogenation") describes a suitable noble metal catalyst and mild conditions. Other suitable catalysts are detailed, for example, in U.S. Pat. No. 4,157,294 to Iwao et al. ("Method of Preparing Base Stocks for Lubricating Oil"), and U.S. Pat. No. 3,904,513 to Fischer et al. ("Hydrofinishing or Petroleum"). The nonnoble metal (such as nickel-molybdenum) hydrogenation metal are usually present in the final catalyst composition as oxides, or more preferably or possibly, as sulfides when such compounds are readily formed from the particular metal involved. Preferred non-noble metal overall catalyst compositions contain in excess of about 5 weight percent, preferably about 5 to about 40 weight percent molybdenum and/or tungsten, and at least about 0.5, and generally about 1 to about 15 weight percent of nickel and/or cobalt determined as the corresponding oxides. The noble metal (such as platinum) catalysts contain in excess of 0.01% metal, preferably between 0.1 and 1.0% metal. Combinations of noble metals may also be used, such as mixtures of platinum and palladium.

The hydrogenation components can be incorporated into the overall catalyst composition by any one of numerous procedures. The hydrogenation components can be added to matrix component by co-mulling, impregnation, or ion exchange and the Group VI components, i.e.: molybdenum and tungsten can be combined with the refractory oxide by impregnation, co-mulling or co-precipitation. Although these components can be combined with the catalyst matrix as the sulfides, that is generally not the case. They are usually added as a metal salt, which can be thermally converted to the corresponding oxide in an oxidizing atmosphere or reduced to the metal with hydrogen or other reducing agent. If necessary, the non-noble metal composition can then be sulfided by reaction with a sulfur donor such as carbon bisulfide, hydrogen sulfide, hydrocarbon thiols, elemental sulfur and the like.

The matrix component can be of many types including some that have acidic catalytic activity. Ones that have activity include amorphous silica-alumina or may be zeolitic or non-zeolitic crystalline molecular sieves. Examples of suitable matrix molecular sieves include zeolite Y, zeolite X and the so-called ultra stable zeolite Y and high structural silica alumina ratio zeolite Y such as, for example, described in U.S. Pat. No. 4,401,556 to Bezman, et al. ("Midbarrel Hydrocracking"), U.S. Pat. No. 4,820,401 to Partridge, et al. ("Hydrocracking Process with Improved Distillate Selectivity with High Silica Large pore Zeolites"), and U.S. Pat. No. 5,059,567 to Listen, et al. ("Process for the Preparation of a Modified Zeolite"). Small crystal size zeolite Y, such as described in U.S. Pat. No. 5,073,530 to Bezman, et al. ("Hydrocracking Catalyst and Process") can also be used. Non-zeolitic molecular sieves which can be used include, for example, silicoaluminophosphates (SAPOs), ferroaluminophosphate, titanium aluminophosphate and the various ELAPO molecular sieves described in U.S. Pat. No. 4,913,799 to Gortsema, et al. ("Hydrocracking Catalysts and Processes Employing Non-Zeolitic Molecular Sieves") and the references cited therein. Details regarding the preparation of various non-zeolite molecular sieves can be found in U.S. Pat. No. 5,114,563 to Lok, et al. ("Hydrocarbon Conversions Using Catalysts Silicoaluminophosphates"): and in U.S. Pat. No. 4,913,799 . Mesoporous molecular sieves can also be included, for example the M41 S family of materials, MCM-41 (U.S. Pat. No. 5,246,689 to Beck, et al. ("Synthetic Porous Crystalline Material Its Synthesis and Use"), U.S. Pat. No. 5,198,203 to Kresge, et al. ("Synthetic Mesoporous Crystalline Material"), and U.S. Pat. No. 5,334,368 to Beck, et al. ("Synthesis of Mesoporous Oxide")), and MCM-48.

Suitable matrix materials may also include synthetic or natural substances as well as inorganic materials such as clay, silica and/or metal oxides such as silicaalumina, silica-magnesia, silica-zirconia, silica-thoria, silica-berylia, silica-titania as well as ternary compositions, such as silica-alumina-thoria, silica-alumina-zirconia, silica-alumina-magnesia, and silica-magnesia zirconia. The latter may be either naturally occurring or in the form of gelatinous precipitates or gels including mixtures of silica and metal oxides naturally occurring clays which can be composited with the catalyst include those of the montmorillonite and kaolin families. These clays can be used in the raw state as originally mined or initially subjected to calumniation, acid treatment, or chemical modification.

An adsorption step may be used to remove nitrogenous or sulfurous compounds from the product. The use of adsorption is generally described, for example, by Gruse and Stevens, Chemical Technology of Petroleum, 3rd ed., McGraw Hill Book Company, Inc., NY (1960 ), and Day, Proc. Am. Phil. Soc., 36:112 (1897), the contents of which are hereby incorporated by reference.

Suitable adsorbents for nitrogen-containing compounds are well known to those of skill in the art, and include heteroatom acid materials such as acidic clays, molecular sieves, and ion exchange resins. Such materials are described, for example, in U.S. Pat. No. 4,657,661 to Miller, the contents of which are hereby incorporated by reference. Bauxite and alumina can also be used. Adsorbents for sulfur-containing compounds are also well known.

An extraction step can be used to remove heteroatom-containing species from the feedstock. The use of solvents to selectively extract nitrogen compounds from hydrocarbons is well known to those of skill in the art, and is described, for example, in Gruse and Stevens, ibid, p. 332. Gruse and Stevens describe, for example, that nitrogen compounds are preferentially dissolved in many common solvents, including N-methyl pyrrolidone, phenol, fiurfural, nitrobenzene, and sulfur dioxide. Phenol, furfural and N-methyl pyrrolidone are used more commonly, but since N-methyl pyrrolidone contains nitrogen itself, care must be taken to ensure that the feedstock has been adequately stripped of N-methyl pyrrolidone.

Any number of commercially available apparatus, including those based on chemiluminescence and gas chromatography, may be used to monitor the nitrogen content of the nitrogen-containing, substantially paraffinic Fischer-Tropsch products (and the feedstocks to and products of a denitrification step), according to the methods described herein. Commercial analyzers based on chemilumininesce and associated equipment are sold, for example, by Antek Instruments, Inc. (Houston, Tex.) and are described at least in U.S. Pat. Nos. 4,018,562 and 4,351,801, the contents of which are hereby incorporated by reference. Similarly, Fisons Instruments S.p.A (Milan, IT) supplies analyzers based on chromatography. Such instruments are described at least in U.S. Pat. No. 5,612,225, the contents of which are hereby incorporated by reference. The monitoring can be done continuously or periodically, as desired.

One method for determining the nitrogen content of a hydrocarbon sample involves pyrolysis of the hydrocarbon to yield pyrolysis gases, which include carbon dioxide, water, and nitric oxide. The nitric oxide is hydrogenated at high temperatures in the presence of a nickel catalyst to form ammonia. The resulting ammonia can be coulometrically titrated, for example, using a four-electrode hydrogen cell. Systems based on these methods are known as micro-coulometric titrating systems. This technique is described, for example, in U.S. Pat. No. 3,032,493, the contents of which are hereby incorporated by reference.

Chemiluminescence is a more preferred method for determining nitrogen content. Chemiluminescent detection equipment for detecting chemically-bound nitrogen is based on the reaction of nitric oxide with ozone to form metastable nitrogen dioxide ($NO_2$ *), which instantaneously relaxes to its ground state with a resulting photo-emission of light energy ($\upsilon$). The chemiluminescent detection is based on this photo-emission of light energy. The emitted light is detected by a photo-multiplier tube whose output is an electrical potential proportional to the intensity of the light detected. Appropriate electronic circuitry may be provided to convert the electrical potential output of the photo-multiplier tube to an analog electrical signal for driving a chart recorder and for application to an integrator for deriving and displaying a digital count that is proportional to the quantitative value of the chemically-bound nitrogen contained in the sample.

The chemical reactions are shown as follows:

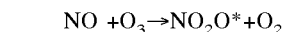

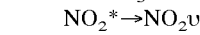

The nitric oxide is generated from the initial Fischer-Tropsch wax by pyrolyzing the wax in an oxygen-rich gas to form pyrolysis gases, which include nitric oxide, carbon dioxide and water. The water is removed, and the nitric oxide is reacted with ozone.

The chemiluminescent detection of nitrogen is well known to those of skill in the art, and is described, for example, in U.S. Pat. No. 4,018,562 to Parks, et al., the contents of which are hereby incorporated by reference. The chemiluminescent nitrogen detectors are commonly known as NO/NOR detectors. Using the devices and methods described in U.S. Pat. No. 4,018,562, several solid and liquid samples can be analyzed.

The analysis of Fischer-Tropsch waxes using the suggested procedures for handling solid materials as described in U.S. Pat. No. 4,018,562 does not provide reproducible results. While not wishing to be bound to a particular theory, it is believed that the types of solids which can be effectively analyzed are those which form a residue and which do not boil, spatter or bump during analysis. Erratic results are obtained if the solid materials boil and spatter during the analysis. Fischer-Tropsch waxes are an example of solid materials which boil and spatter during the analysis. Accordingly, the methods described herein were developed to overcome this limitation.

The sulfur content of samples of Fischer-Tropsch wax and other heavy products can be obtained using a gas chromatograph equipped with a flame ionization detector, a wide-bore fused-silica capillary column, direct injector, and a sulfur chemiluminescence detector. Determination of sulfur content using this methodology is well known to those of skill in the art. An example of a suitable pulsed fluorescence detector assembly suitable for use in this analysis is sold by Thermo Environment Instruments Inc. of Franklin, Mass. as a "Model 43 Pulsed Fluorescence $SO_2$ Analyzer."

Oxygen-containing compounds (oxygenates), while not as problematic as sulfur- or nitrogen-containing compounds, may be of some concern if they are present in various products, and may also need to be removed. Chromatographic methods for determining oxygen content, in particular, using GC/MS techniques, are well known to those of skill in the art, and are not described in more detail here.

The methods described herein will be better understood with reference to the following non-limiting examples. While the examples are described with respect to nitrogen impurities, the methods described herein apply to other heteroatom impurities, such as sulfur and oxygen impurities.

EXAMPLE 1

Solubility of Fischer-Tropsch Wax

Attempts were made to dissolve Fischer Tropsch wax in a series of solvents following a standard method used to dissolve petroleum waxes. The solvents used were solvents which typically dissolve petroleum waxes. However, none of these solvents was suitable for dissolving Fischer Tropsch wax. The Fischer-Tropsch wax product was insoluble in iso-octane, toluene, and xylene, and only partially dissolved in cyclohexane.

EXAMPLE 2

Analysis of Nitrogen Content via Chemiluminescence

Samples of nitrogen containing Fischer Tropsch wax were analyzed via an ANTEK9000 Series Nitrogen/Sulfur Analyzer. Methods for performing the assay are relatively straightforward, and are disclosed, for example, in U.S. Pat. No. 4,018,562.

The apparatus used was an Antek 9000 total nitrogen and sulfur analyzer equipped with a vacuum pump. The devices included a Model 735 controlled rate sample drive, a Model 740 Multi-Matrix Sample inlet, an IBM compatible personal computer with Antek software, an HP laser jet printer, a Mettler MT5 balance capable of weight to 0.1 mg, sample boats for solid samples, and a source of helium and oxygen. The apparatus was prepared according to SOP EQ-125-0 from Antek, using attachments 1–4 to set up instrument control parameters, time functions and autosampler control. The instrument was calibrated using known standards. Typical sample weights for analysis ranged from between 5 and 25 mg. A standard test method for determining trace nitrogen in liquid petroleum hydrocarbons is ASTM D 4629, published in 1996.

The manufacturer's recommendations regarding solid samples were followed. The recommended procedure was to directly inject the solid samples into the instrument. Two analyses were run on the same sample. Each analysis was performed by placing a samples of a nitrogen containing Fischer Tropsch wax in boats and injecting the sample into an ANTEK9000 Series Nitrogen/Sulfur Analyzer. Although the samples were identical, the analysis showed the nitrogen content (PPM) as 41.60 and 116.5. This shows a relatively large amount of variation, showing that there is an unacceptable accuracy using the recommended procedure.

Three additional analyses were run on the same sample of material, following the above procedure, except that the boats were held at the mouth of the combustion chamber for a sufficient amount of time to permit the sample to melt before entering the combustion zone. This caused the sample to melt before being exposed to extremely heat, and minimized any spattering/boiling of the sample. The resulting analyses showed nitrogen contents (PPM) of 30.28, 29.41 and 32.83. This data shows that much greater repeatability can be obtained using the methods described herein.

The invention has been described with respect to particularly preferred embodiments. Modifications obvious to the ordinary skilled artisan are intended to be included within the invention and claims.

What is claimed is:

1. A method of determining the heteroatom content of a room-temperature solid obtained from a Fischer Tropsch synthesis, comprising:
    a) melting the solid; and
    b) performing an analysis which determines the heteroatom content of the melted sample.

2. The method of claim 1, wherein the analysis is selected from the group consisting of chemiluminescence, chromatographic methods, GC/MS, and combinations thereof.

3. The method of claim 2, wherein the method is chemiluminescence.

4. The method of claim 3, wherein the analysis after melting follows ASTM D 4629-96.

5. The method of claim 1, wherein the heteroatoms are nitrogen or sulfur.

6. The method of claim 1, wherein the solid samples are loaded on boats prior to melting and analysis.

7. The method of claim 1, wherein the analysis involves chemiluminescence.

8. The method of claim 1, wherein the analysis involves chromatography.

9. The method of claim 1, wherein the solid sample is wax directly obtained from a Fischer-Tropsch synthesis or is distilled from a portion of the product of a Fischer-Tropsch synthesis.

10. The method of claim 1, wherein the solid is wax from a Fischer-Tropsch synthesis that has been hydrogenated.

11. The method of claim 1, wherein the solid is wax from a Fischer-Tropsch synthesis that has been denitrified.

12. The method of claim 1, wherein the solid is wax from a Fischer-Tropsch synthesis that has been hydrocracked.

13. The method of claim 1, wherein the solid is wax from a Fischer-Tropsch synthesis that has been hydrodesulfurized.

14. The method of claim 3, further comprising adjusting the Fischer-Tropsch process to reduce the heteroatom content.

15. The method of claim 10, further comprising adjusting the hydrogenation conditions to reduce the heteroatom content.

16. The method of claim 11, further comprising adjusting the denitrification conditions to reduce the heteroatom content.

17. The method of claim 12, her comprising adjusting the hydrocracking conditions to reduce the heteroatom content.

18. The method of claim 13, further comprising adjusting the hydrodesulfrrization conditions to reduce the heteroatom content.

19. A process for preparing a solid hydrocarbon material from Fischer-Tropsch synthesis, wherein the material includes nitrogen impurities, comprising:
   a) subjecting syngas to Fischer-Tropsch synthesis,
   b) isolating a solid hydrocarbon material from the Fischer-Tropsch synthesis, and
   c) analyzing the solid hydrocarbon material for heteroatom content by:
      i) melting the solid; and
      ii) performing an analysis which determines the heteroatom content of the melted sample.

20. The process of claim 19, further comprising adjusting the Fischer-Tropsch synthesis conditions to vary the heteroatom content.

21. The process of claim 20, wherein the Fischer-Tropsch synthesis conditions to be adjusted are selected from pressure, hydrogen/carbon monoxide syngas ratio, temperature, and Fischer-Tropsch catalyst.

22. The process of claim 19, wherein the solid material is analyzed for heteroatom content by chemiluminescence.

\* \* \* \* \*

UNITED STATES PATENT AND TRADEMARK OFFICE
CERTIFICATE OF CORRECTION

PATENT NO. : 6,503,956 B2
DATED : January 7, 2003
INVENTOR(S) : Nga Malekzadeh

It is certified that error appears in the above-identified patent and that said Letters Patent is hereby corrected as shown below:

<u>Title page,</u>
Item [75], Inventors, change "Nga Maleksadeh" to -- Nga Malekzadeh --

<u>Column 9,</u>
Line 17, change "her" to -- further --
Line 18, change "hydrodesulfrrization" to -- hydrodesulfurization --

Signed and Sealed this

Tenth Day of June, 2003

JAMES E. ROGAN
*Director of the United States Patent and Trademark Office*